United States Patent
Bayer et al.

(10) Patent No.: US 10,154,865 B2
(45) Date of Patent: Dec. 18, 2018

(54) ORTHOPEDIC IMPLANTS, PARTICULARLY BONE SCREWS, AND METHODS FOR PRODUCING SAME

(71) Applicant: BIOTRONIK AG, Buelach (CH)

(72) Inventors: Ullrich Bayer, Bad Doberan (DE); Daniel Lootz, Rostock (DE)

(73) Assignee: BIOTRONIK AG (CH)

( * ) Notice: Subject to any disclaimer, the term of this patent is extended or adjusted under 35 U.S.C. 154(b) by 320 days.

(21) Appl. No.: 15/059,553

(22) Filed: Mar. 3, 2016

(65) Prior Publication Data

US 2016/0278829 A1 Sep. 29, 2016

Related U.S. Application Data

(60) Provisional application No. 62/137,239, filed on Mar. 24, 2015.

(51) Int. Cl.

| A61B 17/84 | (2006.01) |
|---|---|
| A61L 31/02 | (2006.01) |
| A61L 31/08 | (2006.01) |
| A61L 31/14 | (2006.01) |
| A61L 31/16 | (2006.01) |
| A61B 17/86 | (2006.01) |
| A61B 17/56 | (2006.01) |

(52) U.S. Cl.
CPC ............ *A61B 17/846* (2013.01); *A61B 17/86* (2013.01); *A61B 17/863* (2013.01); *A61B 17/864* (2013.01); *A61B 17/866* (2013.01); *A61B 17/8625* (2013.01); *A61L 31/022* (2013.01); *A61L 31/08* (2013.01); *A61L 31/14* (2013.01); *A61L 31/16* (2013.01); *A61B 2017/561* (2013.01); *A61L 2300/414* (2013.01); *A61L 2430/02* (2013.01)

(58) Field of Classification Search
CPC ........ A61B 17/846; A61B 17/84; A61B 17/86
See application file for complete search history.

(56) References Cited

U.S. PATENT DOCUMENTS

| 5,348,026 A | 9/1994 | Ando | |
|---|---|---|---|
| 8,075,562 B2 * | 12/2011 | Murphy | ................. A61B 17/80 424/484 |
| 2014/0243911 A1 * | 8/2014 | Almarza | ............ A61B 17/8605 606/305 |

FOREIGN PATENT DOCUMENTS

WO WO 94/07425 A1 4/1994

OTHER PUBLICATIONS

European Search Report, 16158658.1-1455, dated Aug. 30, 2016.

* cited by examiner

*Primary Examiner* — Andrew Yang
(74) *Attorney, Agent, or Firm* — Craig A. Fieschko, Esq.; DeWitt Ross & Stevens S.C.

(57) ABSTRACT

An orthopedic implant, such as a bone screw with a self-tapping thread, is formed of a biodegradable material such as a magnesium alloy. A bioactive surface coating is provided on the implant, such as at the threading. The coating contains micro-abrasives which assist with screw/implant penetration, and/or contains microcapsules containing lubricant, wherein the microcapsules rupture from pressure and frictional heat as the implant penetrates bone.

20 Claims, 2 Drawing Sheets

ORTHOPEDIC IMPLANTS, PARTICULARLY BONE SCREWS, AND METHODS FOR PRODUCING SAME

CROSS-REFERENCE TO RELATED APPLICATIONS

This application claims priority under 35 USC § 119(e) to U.S. Provisional Patent Application 62/137,239 filed 24 Mar. 2015, the entirety of which is incorporated by reference herein.

FIELD OF THE INVENTION

The invention relates to orthopedic implants, particularly a bone screw with self-tapping thread, and to methods for producing such implants.

BACKGROUND OF THE INVENTION

Bone screws with self-tapping threads have been known for decades and constitute key fastening elements in the field of prosthetics. During their long period of use, such bone screws have been the subject of many improvements, both in terms of their materials and their geometric configuration. High-grade steel and titanium screws have enjoyed the most widespread use in the past. However, efforts are continually being made to provide orthopedic implants of different materials with comparable performance characteristics. In this regard, bone screws made of Mg (magnesium) alloys are known (see, e.g., US 2011/0313527 A1), and also screws based on magnesium with special coatings (see, e.g., US 2012/0150295 A1).

Magnesium has lower strength than titanium and high-grade steel. This makes the use of magnesium problematic for self-tapping resorbable bone screws that have to be introduced into bone tissue with high torque. Particularly in the case of small-scale and/or cannulated screws, there is the risk that the torque to be applied will exceed the torsional strength of the material, and that the screw will thus be over-tightened and will break.

SUMMARY OF THE INVENTION

The invention seeks to provide a bone screw or other orthopedic implant (e.g., nail, staple, etc.) with reduced failure risk and the possibility of further miniaturization, as well as a method for producing implants of this type.

The invention reduces friction when screwing in or otherwise installing the implant as a result of a surface functionalization of the implant surface, e.g., the thread profile of a screw implant. The necessary torque or torsional moment is thus decreased, and the risk of screw fracture is considerably reduced. Preferred versions of the invention further involve a surface-functionalized, self-tapping and self-lubricating thread profile wherein bioactive substances accelerating bone growth/healing, such as bone morphogenetic proteins (which promote proliferation of human bone cells), are released during and immediately after the tapping process. The thread thus has a multi-functional surface. The invention may also or instead utilize a localized additive, preferably in the form of micro-abrasives in the bioactive surface coating, to increase the self-tapping effect.

The implant is preferably formed of magnesium (Mg) or other biodegradable compounds, with the implant's surface roughness being increased by adhered and/or embedded abrasives which enhance the surface's ability to cut/penetrate bone. Additionally, polymeric hollow spheres or other microcapsules are preferably embedded in or adhered to the surface, with the microcapsules containing bioactive materials (e.g., substances promoting bone growth, preferably in liquid or pasty form) to assist with the implant's integration and absorption into the body, and/or lubricant to assist with further reducing the torque/force needed for installation of the implant.

When the implant is provided in the form of a screw which is tapped/screwed into cancellous bone, local frictional moment is produced at the thread crests and the thread flanks. This results in fragmentation of the adhered and/or embedded abrasives (which are preferably hard and brittle), and also generates localized frictional temperature increases. Both effects assist with rupture of the microcapsules, resulting in release of the bioactive ingredients and/or lubricant.

Due to the improved tapping efficacy provided by the abrasives and/or the lubricant, friction is minimized during the screwing-in process. The associated lower torsional load on the screw allows reduction of its cross-sectional area, and thus reduction of its mass. Mass reduction considerably contributes to reduction of the implant's degradation time in the body, and reduces the quantity of released hydrogen (a known problem in Mg implants). The implant therefore has greater biocompatibility and reduced patient rehabilitation time. Since implant size/mass can be reduced, the invention offers new fields of use for resorbable implants, e.g., in the skull and small limb field.

In an exemplary version of the implant, a bone screw has a hollow/cannulated main body with an outer diameter of 1.5-5 mm, between 2.5-3.5 mm being preferred, and an inner diameter in the range between 0.5-2.5 mm, between 0.8-1.3 mm being preferred. The reduction of the quantity of magnesium provided by the cannulation promotes reduced degradation time, and reduced hydrogen release during degradation. Reduction of hydrogen release reduces the risk of pocket-like deposition of hydrogen, where the hydrogen cannot be resorbed quickly enough by the body.

In some versions of the implant, the micro-abrasives of the surface coating can be destroyed, in particular can be converted into smaller particles, by pressure and frictional heat as the implant is screwed or otherwise urged into bone, whereby the particles effectively enlarge the implant's surface area. This increases the effective tapping ability of the implant with respect to the bone tissue. This in turn allows a possible reduction of implant dimensions, with the aforementioned advantages. The smaller particles forming from the larger abrasives additionally allow the implant to grow more quickly into the bone matrix.

The micro-abrasives may include crystalline hydroxyapatite, preferably formed as needle-shaped particles. The typical commercially-available form of this material is particularly suitable, particularly if the abrasive particles in the surface coating are oriented to increase the tapping ability and edge-holding ability of the proposed bone screw.

The microcapsules (when provided) may contain bone morphogenetic proteins or other bioactive material promoting bone healing and growth. The implant surface then begins to interact with the bone substance immediately as the implant penetrates the cancellous bone. The frictional heat and the fragmentation of the abrasive material produced during the insertion process activate the bone morphogenetic proteins, which immediately come into contact with the spongiosa on the one hand and the implant material on the other hand.

The microcapsules may have a biopolymer shell, preferably including a polylactide, and most preferably including a polylactic acid (PLA) blend. These are easily and economically available shell materials which are well suited for a biodegradable product.

Preferably, the microcapsules and/or the micro-abrasives have a (major) dimension between 0.2 and 20 µm, in particular between 1 and 10 µm. With these dimensions, highly effective functional coatings of screws of all practically significant dimensions can be produced with established coating techniques, and the coatings are on the one hand sufficiently effective and on the other hand sufficiently stable.

Where the implant is a screw or otherwise threaded, the thread preferably has a fine knife-like profile. Other thread profiles/cross sections are possible, such as threads with curved flanks, though such configurations may not be preferable owing to greater production complexity.

An exemplary method of producing an orthopedic implant, in particular a bone screw, of the aforementioned type includes the steps of:
(1) providing a main body, for example a tube, from a degradable alloy (e.g., magnesium):
(2) shaping a thread in the outer wall of the main body in order to produce the bone screw (or the bone screw portion of the orthopedic implant),
(3) forming a coating base on at least a portion of the surface of the thread, and
(4) applying/introducing the micro-abrasives and/or the microcapsules to and/or into the coating base.

The implant, or the main body thereof, could be produced using other methods (e.g., casting or pressure die casting methods), but machining the threads therein is typically most cost-effective. Preferred methods of thread formation are rotary extrusion with subsequent milling or grinding, or milling or thread cutting.

The coating base may be formed by immersion in a coating liquid, preferably a liquid containing a polylactide (especially a PLA blend), and subsequent drying at elevated temperature (that is, higher than ambient temperature). Spray-coating and other known liquid-coating methods are also possible. Application of micro-abrasives may also be done via immersion in a liquid containing micro-abrasives with subsequent drying at elevated temperature. Similarly, application of microcapsules may be done via immersion in a liquid containing microcapsules with subsequent drying at elevated temperature. Prior to application of micro-abrasives or microcapsules, the surface of the implant may be etched to create a micro-rough adhesive surface, or otherwise roughened, for better adhesion of the micro-abrasives or microcapsules.

DETAILED DESCRIPTION OF EXEMPLARY VERSIONS OF THE INVENTION

Figure 1A:
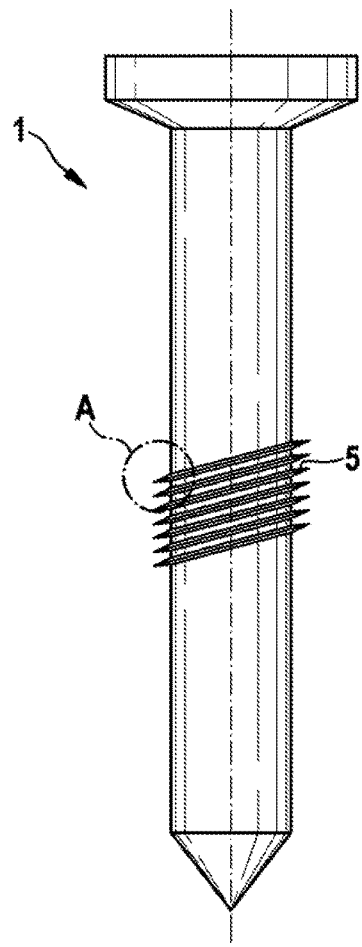
FIGS. 1A to 1C show illustrations of an exemplary bone screw according to the invention and of an associated cross pin for screwing in the bone screw.
Figure 1B:
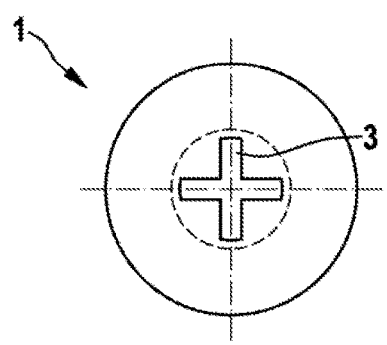
Figure 1C:
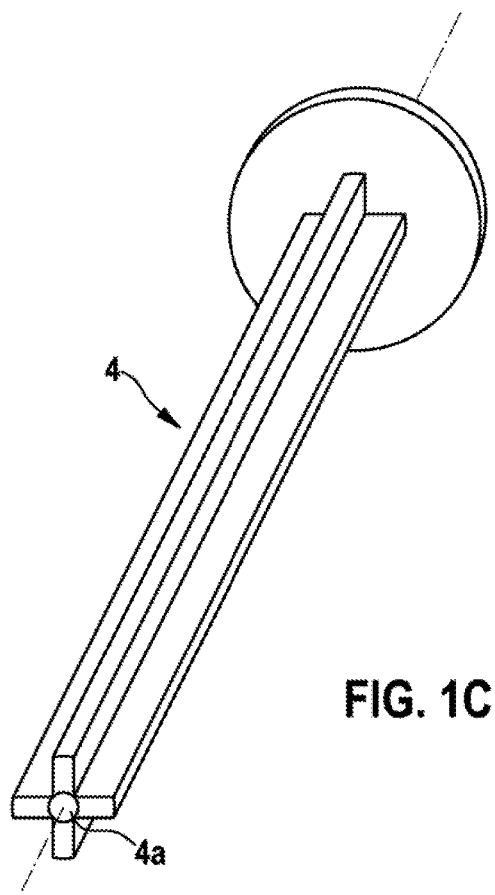

FIG. 1A shows a side view of a bone screw 1 made of an Mg alloy, which is cannulated (internally hollow). More specifically, referring to the plan view of the screw head in FIG. 1B, the bone screw 1 has a non-circular—here cruciform—internal passage 3. FIG. 1C is a perspective illustration of a pin 4 having a cruciform cross-section which complementarily fits into the internal passage 3 of the bone screw 1, wherein a longitudinal bore 4a is provided in the pin 4 for insertion of a guide wire.

The configuration described has the advantage that the bone screw can be manufactured with lesser material, thereby providing less material that corrodes and that is to be broken down in the body. The hollow profile bearing the non-circular internal passage, in conjunction with the use of the cross pin (which is preferably manufactured from a steel or titanium alloy) makes it possible to transfer higher torques as the screw is screwed in compared with a solid (non-hollow) bone screw manufactured from a Mg alloy.

Figure 2:
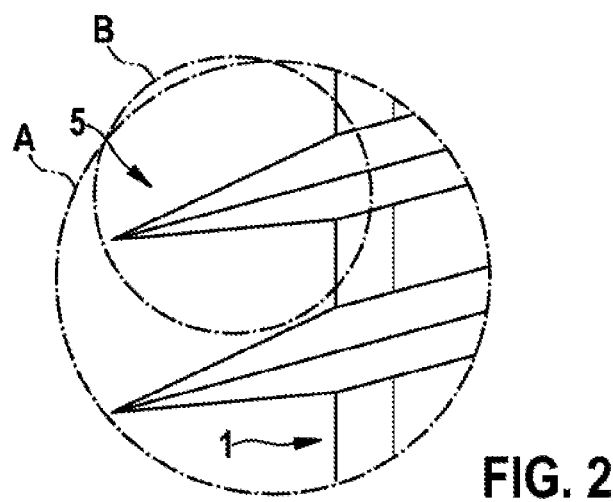
FIG. 2 shows a detailed view from FIG. 1A.

FIG. 2 shows the detail A from FIG. 1A, illustrating the screw thread 5 of the bone screw 1 in greater detail. The thread profile is a very "sharp" one with an acute angle between the flanks of the thread, with the illustrated version having an angle between the thread flanks of approximately 20°. Other angles are possible, with angles of 15°–30° being preferred depending on the specific material and purpose of the screw.

Figure 3A:
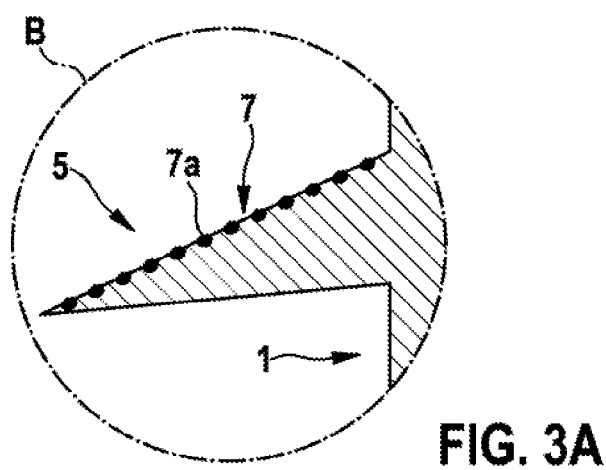
FIGS. 3A and 3B show detailed views, adapted from FIG. 2, of versions of the invention.
Figure 3B:
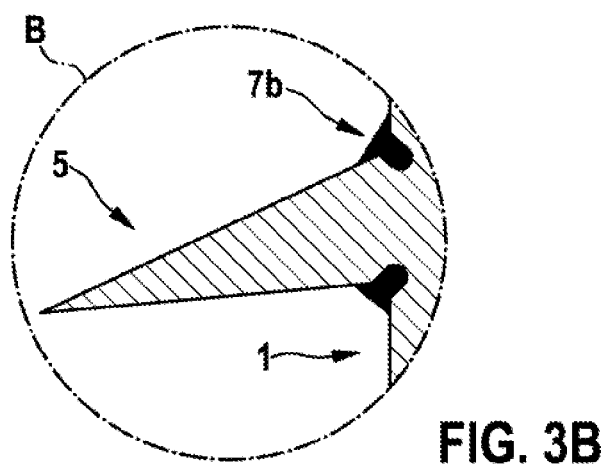

FIG. 3A shows the detail B from FIG. 2 in a sectional view, illustrating a surface coating 7 with deposited micro-abrasives 7a "anchored" in cavities of the thread flank of the screw thread 5. The further detailed view of FIG. 3B shows an alternative or additional arrangement, with the surface coating 7 of FIG. 3A omitted, wherein micro-reservoirs (microcapsules) 7b are situated where the thread flanks meet the thread roots. These microcapsules 7b are formed of a biodegradable polymer shell filled with a lubricant (which assists with bone penetration by the screw thread 5), and may also contain a medical active ingredient (e.g., for osteosynthesis) where appropriate. The microcapsules 7b of FIG. 3B can be combined with the micro-abrasives 7a shown in FIG. 3A, or either of the micro-abrasives 7a and microcapsules 7b can be used individually.

The thin surface coating 7 is preferably a biodegradable polymer which acts as a host matrix for the micro-abrasives 7a, which can be formed from hydroxyapatite (bone mineral). The microcapsules 7b can be deposited along with the surface coating 7 to adhere to the thread surface in an integrally bonded and form-fitting manner, or they can otherwise be attached to the surface of the thread 5 (preferably within cavities in the thread surface, and preferably being covered with microcrystalline hydroxyapatite after their placement). When the surface coating 7 is applied with both the micro-abrasives 7a and the microcapsules 7b, a surface composite results with hard hydroxyapatite crystals and microcapsules deposited therebetween. The micro-abrasives 7a assist with cutting and penetrating bone, and the microcapsules 7b assist with lubrication and reduction in the applied torque needed for penetration.

During the tapping process, the microcapsules 7b are destroyed mechanically, and also by thermal effects (microfrictional heat) by the fragmentation of the hard and brittle hydroxyapatite bodies (where present). The released lubricant, which can merely be a viscous carrier liquid loaded with active ingredient, results in a self-lubricating effect which further reduces the torque needed to screw in the screw. Due to the reduction of the screw-in torque, the screw experiences lower torsional loading. This allows reduction in the wall thickness of the cannulated screw, and thus in the mass of the screw (typically by 20% to 50%). The invention therefore allows further miniaturization of bone screws without increased risk of screw breakage owing to the torsional load. Further miniaturization also shortens the screw's degradation period, and reduces the quantity of hydrogen released by the screw as it degrades.

Hydroxyapatites belong to the group of calcium phosphates, which (as bone replacement materials) do not cause any endogenous defensive reactions. Hydroxyapatites, however, are brittle. This is expressed by low fracture toughness characteristic values ($K_{IC}$=MPam$^{1/2}$). For this reason hydroxyapatites are generally not used for load-bearing orthopedic implants, as they are susceptible to crack formation and lack mechanical durability.

Where the invention utilizes hydroxyapatites, it utilizes this alleged disadvantage rather selectively. The hydroxyapatite crystals (with a particle size range of, for example, 1-5 μm) deposited on and/or in the magnesium matrix of the screw are exposed to complex mechanical loads—tensile, compressive, and torsional stresses—during the screw-in process. These complex stresses exceed the strength of the hydroxyapatite crystals, thus resulting in their fragmentation. Microcrystalline particles (for example, 0.1-1 μm in diameter) with much greater actual surfaces are produced, with some remaining anchored in the magnesium surface of the screw, and others being shed from the surface and into the surrounding cancellous bone (with assistance from the liquid contained in the microcapsules, where present).

Thus, to review, the screwing of the screw into the cancellous bone is facilitated by the tapping effect of the hydroxyapatite crystals (which are still large at this stage of the screw's installation). The lower torque needed to screw in the screw protects against over-tightening of the screw. The fragmentation of the hydroxyapatite crystals during screw-in produces smaller particles and exposes greater surface area, making the calcium phosphate of the hydroxyapatite crystals more biologically available. This provides a higher degree of bioactivation via local synthesis of a bioactive composite, particularly when it occurs in conjunction with the release of the carrier liquid loaded with active substance, and the availability of the fragments of the degradable capsule material. The composite stimulates a much earlier formation of osteoblasts, resulting in quicker formation of new bone substance.

The foregoing arrangement can be modified by admixing amorphous titanium oxide powder (TiO2) with the microcrystalline particles (preferably having 1-5 μm diameter) in a concentration of, for example, 5-10% by mass. The particle size of the titanium oxide powder is preferably between 50 and 100 nm in diameter. Again, as the bone screw is screwed into the spongiosa, the hydroxyapatite deposited in or on the thread surface assists in tapping, and also experiences fragmentation. The torsional moment needed to screw the resorbable screw into the bone is reduced (or at least maintained), reducing the risk of overtightening the screw before the required screw-in depth has been reached. Tapping produces active spongiosa surfaces which demonstrate increased biological interaction with the hydroxyapatite, accelerating integration of the screw surface. The bio-inert nanoscale titanium oxide powder assists with fragmentation of the hydroxyapatite crystals and further accelerates screw absorption. The titanium oxide, which does not influence degradation of the screw, remains in the gaps of the spongiosa.

Details of implementation of an exemplary version of the invention follow:

1. An extruded tube made of the biodegradable Mg alloy WE 43, having OD=2.5 mm, ID=0.8 mm, and a resultant wall thickness=0.85 mm, is provided.
2. A screw main body, having a length from 15 mm to 40 mm, is detached.
3. A self-tapping fine-thread profile is mechanically cut into the tube with a threading die, with thread depths from 0.5 to 0.7 mm and a thread pitch between 0.5 and 1.5 mm/revolution.
4. The screw is cleaned in isopropanol (residence time 2 min).
5. The screw is immersed (dip coating) in a liquid formed of polylactic acid (PLA) or PLA blend containing hydroxyapatite particles (particle size between 1 and 10 μm), at 150° C. or more.
6. The screw is dried in a convection oven at temperatures between 60 and 80° C.
7. The coated screw is briefly immersed (<10 s) in chloroform. As a result, part of the surface is etched, leaving microcavities
8. The screw is then removed and immersed (10-30 s) in an aqueous liquid containing microcapsules. These microcapsules, having a diameter between 1 and 10 μm, have a shell made of a PLA or PLA blend which encapsulates bone morphogenetic proteins.
9. The screw is removed and dried in a convection oven at temperatures between 30 and 40° C. Some of the microcapsules will embed in the microcavities of the surface containing PLA/hydroxyapatite, and/or will adhere fixedly to the screw surface.

The foregoing arrangement can be implemented using other biodegradable alloys, such as the Mg alloys MgCa0.8 or AZ31, and the aforementioned dimensions (the outer and inner diameter of the screw and the resultant wall thickness, the thread depth and pitch and other parameters of the screw configuration, etc.) can be varied.

The versions of the invention described above are merely exemplary, and the invention is not limited to these versions. Rather, the scope of rights to the invention is limited only by the claims set out below, and the invention encompasses all different versions that fall literally or equivalently within the scope of these claims.

What is claimed is:

1. An orthopedic implant having a bone-penetrating portion:
   a. formed primarily of a biodegradable material,
   b. having a surface coating thereon, the surface coating including microcapsules containing at least one of:
      (1) a lubricant, and
      (2) a bioactive substance configured to promote bone growth,
   wherein the microcapsules are configured to rupture as the bone-penetrating portion penetrates bone.

2. The orthopedic implant of claim 1 wherein:
   (1) the surface coating further includes micro-abrasives, and
   (2) the micro-abrasives include crystalline hydroxyapatite.

3. The orthopedic implant of claim 2 wherein the micro-abrasives are needle-shaped.

4. The orthopedic implant of claim 1 wherein the bioactive substance includes bone morphogenetic proteins.

5. The orthopedic implant of claim 1 wherein the microcapsules include a biopolymer shell.

6. The orthopedic implant of claim 5 wherein the biopolymer shell is at least partially formed of a polylactide.

7. The orthopedic implant of claim 1 wherein the microcapsules and/or the micro-abrasives have a maximum dimension between 0.2 and 20 μm.

8. The orthopedic implant of claim 1 wherein the bone-penetrating portion is threaded, whereby the bone-penetrating portion defines a screw.

9. The orthopedic implant of claim 1 wherein the bone-penetrating portion has:
a. a length terminating in a pointed tip, and
b. threading extending from the tip,
whereby the bone-penetrating portion defines a self-tapping screw.

10. The orthopedic implant of claim 1 wherein the bone-penetrating portion is cannulated throughout at least a major portion of its length.

11. The orthopedic implant of claim 10 wherein the bone-penetrating portion has a non-circular internal passage extending throughout at least a major portion of a length of the bone-penetrating portion.

12. The orthopedic implant of claim 11 in combination with a pin configured to complementarily fit within the internal passage, whereby the pin may transmit torque to the bone-penetrating portion.

13. The orthopedic implant of claim 10 wherein the bone-penetrating portion has:
a. a maximum outer diameter between 1.5 and 5 mm, and
b. a maximum inner diameter between 0.5 and 2.5 mm.

14. The orthopedic implant of claim 10 wherein the bone-penetrating portion has:
a. a maximum outer diameter between 2.5 and 3.5 mm, and
b. a maximum inner diameter between 0.8 and 1.3 mm.

15. The orthopedic implant of claim 1 wherein the bone-penetrating portion is defined by a tube:
a. formed primarily of a magnesium alloy, and
b. having a self-tapping thread defined thereon, whereby the bone-penetrating portion defines a bone screw.

16. An orthopedic implant having a bone-penetrating portion:
a. formed primarily of a magnesium alloy,
b. defining a screw having a self-tapping thread defined thereon, wherein at least a portion of surface of the thread bears microcapsules containing at least one of:
(1) a lubricant, and
(2) a bioactive substance configured to promote bone growth,
wherein the microcapsules are configured to rupture as the bone-penetrating portion penetrates bone.

17. A method for producing the orthopedic implant of claim 16, the method including the steps of:
a. providing a member formed primarily of a magnesium alloy;
b. forming a self-tapping thread in an outer wall of the member, whereby the threaded member defines the screw;
c. forming the surface coating on at least a portion of the thread; and
d. providing the microcapsules to the surface coating.

18. The method of claim 17 wherein the step of forming the surface coating includes:
a. immersing at least a portion of the thread in a coating liquid, and
b. subsequent drying at elevated temperature.

19. The method of claim 17 wherein the microcapsules are provided to the surface coating prior to forming the surface coating on at least a portion of the thread.

20. The method of claim 17 further including the step of etching at least a portion of the thread before forming the surface coating thereon.

* * * * *